United States Patent
Bouvier et al.

(10) Patent No.: US 7,693,263 B2
(45) Date of Patent: Apr. 6, 2010

(54) METHOD FOR THE RECONSTRUCTION OF A BODY MAP

(75) Inventors: Bernard Bouvier, Erangy-sur-Oise (FR); Eric Fivel-Demoret, Guyancourt (FR)

(73) Assignee: General Electric Company, Schenectady, NY (US)

( * ) Notice: Subject to any disclaimer, the term of this patent is extended or adjusted under 35 U.S.C. 154(b) by 126 days.

(21) Appl. No.: 11/831,991

(22) Filed: Aug. 1, 2007

(65) Prior Publication Data
US 2008/0031413 A1 Feb. 7, 2008

(30) Foreign Application Priority Data
Aug. 3, 2006 (FR) ................................. 06 53259

(51) Int. Cl.
H05G 1/54 (2006.01)
G01D 18/00 (2006.01)

(52) U.S. Cl. ..................... 378/117; 378/162; 378/197; 378/207

(58) Field of Classification Search ................ 378/117, 378/162, 189, 196, 197, 198, 207
See application file for complete search history.

(56) References Cited

U.S. PATENT DOCUMENTS

| | | | |
|---|---|---|---|
| 5,651,044 A * | 7/1997 | Klotz et al. | 378/117 |
| 5,654,997 A * | 8/1997 | Brownell et al. | 378/117 |
| 5,828,221 A * | 10/1998 | Habraken et al. | 324/662 |
| 6,272,368 B1 * | 8/2001 | Alexandrescu | 600/407 |
| 6,408,051 B2 * | 6/2002 | Habraken et al. | 378/117 |
| 6,412,978 B1 * | 7/2002 | Watanabe et al. | 378/197 |
| 6,661,240 B1 * | 12/2003 | Johnson et al. | 324/662 |
| 6,937,951 B2 * | 8/2005 | Gibb et al. | 702/75 |
| 6,985,556 B2 * | 1/2006 | Shanmugavel et al. | 378/117 |
| 7,130,378 B2 * | 10/2006 | Akutsu et al. | 378/117 |
| 7,172,340 B2 * | 2/2007 | Oota | 378/189 |
| 7,261,464 B2 * | 8/2007 | Noda et al. | 378/197 |
| 7,354,196 B2 * | 4/2008 | Boese et al. | 378/190 |
| 7,428,296 B2 * | 9/2008 | Bernhardt et al. | 378/117 |
| 7,489,142 B2 * | 2/2009 | Somers | 324/661 |
| 7,570,064 B2 * | 8/2009 | Roziere | 324/662 |
| 2006/0097734 A1 | 5/2006 | Roziere | |

FOREIGN PATENT DOCUMENTS

FR 2 844 349 9/2002

* cited by examiner

Primary Examiner—Allen C. Ho
(74) Attorney, Agent, or Firm—Global Patent Operation; Jonathan E. Thomas (57) ABSTRACT

A method and apparatus for reconstructing a body map of a patient that provide automatic control of speeds of moving parts of the apparatus, regulation of an x-ray dose, and computation of time of exposure to the x-ray dose.

11 Claims, 3 Drawing Sheets

METHOD FOR THE RECONSTRUCTION OF A BODY MAP

BACKGROUND

1. Field of the Invention

The field of the present invention relates to a method for the reconstruction of a body map. Embodiments of the present invention can be applied to special advantage but not exclusively in the fields of medical imaging, non-destructive X-ray controls and, more particularly, medical diagnostic apparatuses. The field of the invention also relates to an X-ray apparatus comprising a method of this kind for the reconstruction of a body map.

2. Discussion of Related Art

X-ray diagnostic apparatuses are X-ray image acquisition apparatuses. These apparatuses are used to obtain images, or even sequences or images, of an organ situated inside a living being, especially a human being. An example of an X-ray apparatus such as this is shown in FIG. 1.

Figure 1:
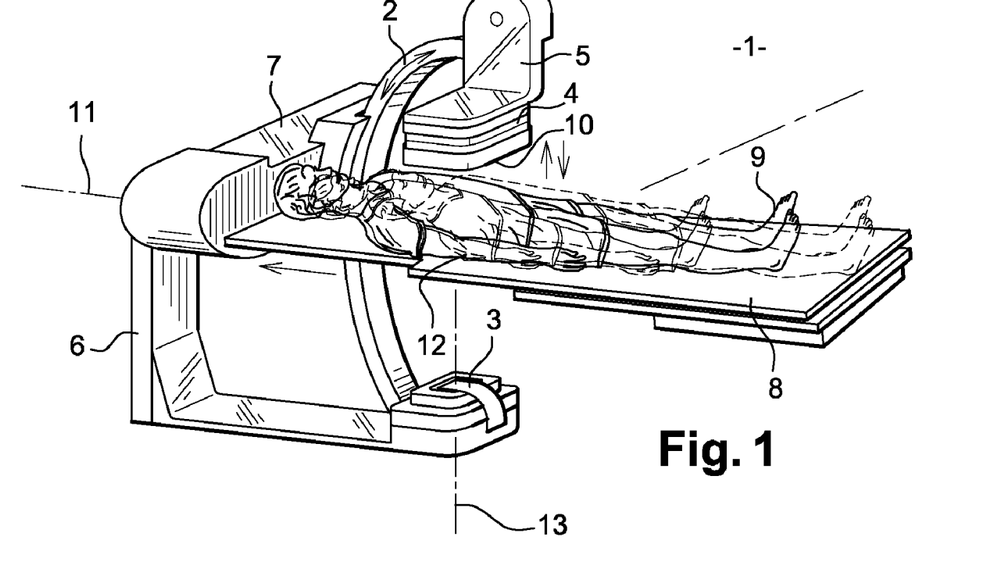
FIG. 1, which has already been described, is a schematic view of a vascular type of X-ray apparatus of the prior art.

The X-ray apparatus of FIG. 1 has moving parts that enable it to rotate in different directions about a patient. These moving parts are capable of moving in all three dimensions of a space. These moving parts generally consist of a C-arm comprising an X-ray tube at one end and a detector at the other end. This tube enables an X-ray beam to be emitted along one direction of emission.

The detector 4 is hooked to the C-arm 2 opposite the tube 3 and in the direction of emission. The detector 4 is connected to a lift device used to raise and lower said detector in the direction of emission.

The C-arm is connected to a post 6 by means of a rotating arm 7 rotating about an axis 11 passing through an isocenter 12 of the X-ray apparatus. The post 6 rotates about an axis 13 passing through the isocenter 12 of the X-ray apparatus.

The X-ray apparatus also has an examination table 8, or a bed, on which a patient 9 reclines. This examination table 8 is placed within the C-arm 2 so that the tube 3 is beneath the examination table and so that the detector 4 is above the examination table.

All three elements, namely the post 6, the rotating arm 7 and the C-arm 2 are hinged relative to one another. This hinging of the post 6, the rotating arm 7 and the C-arm 2 enables the X-ray apparatus 1 to move in three dimensions. This motion of the moving parts of the X-ray apparatus 1 in three dimensions makes it possible to take several images of the organ to be examined at different angles of incidence.

In a radiology examination, the practitioner moves the C-arm 2 and/or the post 6 and/or the rotating arm 7 about the patient 9, especially around the part of the patient's body to be examined. To obtain better quality images, the lift device 5 with the detector 4 is lowered toward the patient. While this lift device is being lowered toward the patient 9, there is a risk that the detector 4 might collide with the patient 9.

To prevent risks of collision with the patient, prior X-ray apparatuses had a model of a virtual volumetric body of a virtual patient in a data base. This model of the virtual patient comprises fixed and simple shapes. The X-ray apparatus also has a model of the different elements of the X-ray apparatus in the data base.

The model of the X-ray apparatus combined with the model of the virtual patient is aimed at slowing down the motion of the moving parts of the X-ray apparatus in the event of a detection of proximity of the virtual patient's body or in the event of contact of one of the elements of the X-ray apparatus with the virtual patient's body. The contact between the model of the X-ray apparatus and the virtual patient does not stop the apparatus but simply slows it down. An anti-collision system 10 therefore has to be associated with the combination of the model of the X-ray apparatus and the model of the virtual patient's body. This anti-collision system 10 may be a proximity detector and/or a contact detector. This anti-collision system stops the motion of the moving parts of the apparatus in the event of contact with the real patient.

However, these prior X-ray apparatuses have drawbacks. During a radiology examination, when the patient's morphology is not the same as the morphology of the virtual patient, there is a very great risk of collision between the detector and the patient.

When the patient's size is smaller than that of the virtual patient, then the slowing down of the motion of the moving parts and the projection of the x-rays are done at a remote distance from the real patient. In this case, the detector is not close enough to the patient to give a high-quality image of the body part undergoing radiography, with a low dose of x-rays.

When the patient's size is greater than that of the virtual patient, then the moving parts get slowed down or stopped when it is too late to prevent collision between the detector and the patient.

With this anti-collision system, the practitioner has to manually reduce the speeds of the C-arm and/or the post and/or the rotating arm in order to reduce the risk of collision between the detector and those parts of the patient that are situated between the detector and the patient when these moving parts are at maximum speed and when the real patient's morphology is greater than that of the virtual patient. The practitioner also has to bring the detector manually closer to the real patient when this real patient's morphology is smaller than that of the virtual patient.

When the moving parts are at maximum speed, the practitioner is constantly afraid of injuring the patient. As a result, the practitioner is under a certain degree of pressure when these moving parts are moving. The practitioner then tends to reduce the speed of the moving parts, even when there is no risk of injuring the patient. This leads to lower productivity in the X-ray machine.

The use of this type of X-ray apparatus is essentially linked to action by the practitioner to control the speeds of the moving parts of the X-ray apparatus. The speed of the moving parts is therefore never at its maximum.

Furthermore the practitioner, who may be a doctor or a nurse or any person likely to use these apparatuses, must be trained to handle the speeds of the moving parts of the X-ray apparatus.

SUMMARY OF THE INVENTION

Embodiments of the invention are aimed precisely at overcoming the above-mentioned, and other, drawbacks of prior systems. To this end, it proposes a method of reconstruction of the contour of the real patient's body, preferably by learning. This reconstruction of the morphology of the real patient liberates the operation from the morphology of the virtual patient as well as the drawbacks entailed in the use of this virtual morphology.

To do this, in addition to the conventional sensors, the detector has an antenna placed in the direction of emission of the x-rays. This antenna has electrodes. At each position of the moving parts around the patient, the electrodes simultaneously measure a distance between the patient's body and the detector. Prior knowledge of the position of the examination table relative to the detector in space makes it possible to assign a measured distance to each electrode of the antenna.

These pieces of data are transmitted to a data base in order to obtain the position and volumetric form of the patient's body map. This provides for real-time knowledge of the position of the moving parts relative to the patient's skin.

Thus, the combination of the motion of the detector with the measurements of the electrodes of the antenna and of the sensors enables the acquisition of a volumetric map of any conductive object placed on the examination table.

This type of reconstruction of a body map makes it possible to dictate a speed on the motion of the moving parts of the x-ray apparatus from the assigned distances. This method of the invention is entirely objective and not subject to action by the practitioner.

The volumetric reconstruction of the patient's body map before the start of the examination reduces the time taken to pre-position the organ to be examined at the isocenter and eliminates the x-ray dose needed for this. pre-positioning operation. The isocenter is the point situated at the intersection between the central axis of the beam and the axis of the rotational motion or curve of the x-ray tube. With the invention, this pre-positioning of the organ at the isocenter is done without using x-rays, thus enabling a reduction of the dose of x-rays received by the patient during an examination.

Similarly, the volumetric reconstruction of patient's body map enables the distance between the detector and the patient's body to be optimized, thereby reducing the x-ray dose received by the patient. The information on the distance between each point of the patient's body and the detector is used to adjust the x-ray dose.

The volumetric reconstruction of the patient's body map is aimed at improving image quality.

In a radiology examination, the volumetric reconstruction of the patient's body map is used to compute the x-ray dose that has accumulated during the radiology examination for each sector of the exposed patient's skin.

The volumetric reconstruction of the patient's body map is aimed at eliminating the preliminary anti-collision test phase before the high-speed acquisition phase.

The volumetric reconstruction of the patient's body map enables the performance of verifications on the patient's position in order to detect any shift between two acquisition phases. This prevents the injection of contrast product if the patient has moved between two phases of an examination that requires a subtraction of images.

More specifically, an embodiment of the invention may provide a method of 3D reconstruction of a body map wherein:

an arm of an x-ray apparatus bearing an x-ray tube and a lift device fixed to a detector is shifted along a trajectory relative to the body, the detector being situated so as to be opposite the tube, the lift device is lowered from the detector towards the body, measurements are made of distances between the detector in the part of the body situated outside the field of the x-rays, using sensors placed on a rim of the detector, the speed of approach of the lift device of the detector relative to the body is automatically controlled according to these measured distances, wherein, measurements are made of distances between the detector and the parts of the body situated in the x-ray field, the measurements of distances between the detector and the parts of the body situated in the x-ray field and the measurements of distances between the detector and the parts of the body situated outside the x-ray field are transmitted to an image learning base which assigns a measured distance to each pixel of the body, the learning base outputs 3D reconstruction parameters of the body map.

Embodiments of the invention may comprise one or more of the following characteristics:

a speed of approach of the detector to the body is computed from the measured distances, the speed of the motions of the lift device of the detector is automatically controlled according to the computed speed of approach and the 3D reconstruction of the body map, a detecting position distance from the detector to the body is automatically controlled according to a risk of collision between the detector and the 3D reconstruction of the body map, depending on the 3D reconstruction of the body map, a thickness of the body is determined, the intensity of the x-rays received by the body is regulated according to the thickness of the body and the distances measured, two measurements are made of distances between the detector and the patient's body without x-ray emission, these measurements are transmitted to the learning base, giving a coarse 3D reconstruction of the body map at output, the organ to be examined is placed at an isocenter of the x-ray apparatus, according to the coarse 3D reconstruction of the body map, the tube or the body is placed in a predetermined position according to the examination to be undertaken.

with the tube, an x-ray beam having a size defined by a collimator of the tube is emitted on a reconstructed body map, a time of exposure of this surface to the x-ray beam is measured, the accumulated dose of x-ray s on said surface is computed according to the measured time of exposure and the size of the x-ray beam, in an examination requiring a subtraction of images, the tube of the body is placed in a position predetermined according to the examination to be undertaken, a first reconstruction of the external envelope of the body is determined, a first radiography image of the body is produced from the x-rays detected by the detector, a second reconstruction of the body map is determined, the first reconstruction of the body map is compared with the second reconstruction of the body map.

if the second reconstruction of the body map has shifted relative to the first reconstruction of the body map, then a new radiography image and a new reconstruction of the body map are determined and this new reconstruction of the body map is compared with the second reconstruction of the body map, and so on and so forth, if not, a contrast product is injected into the body and a second radiography image of the body is determined, the first radiography image is compared with the second radiography image to facilitate medical analysis.

Embodiments of the invention may also provide an x-ray apparatus comprising:

an x-ray tube emitting an x-ray beam along a direction of emission, an x-ray detector situated so as to be opposite the tube and in the direction of emission of the x-rays, a lift device used to raise and lower the x-ray detector in the direction of emission, an arm bearing the detector and the x-ray tube, a post connected to the arm by means of a rotating arm sensors placed on the detector,
wherein
the detector has an antenna situated in the direction of emission of the x-rays,
the apparatus has a circuit for the 3D reconstruction of the patient's body from the learning base, on the basis of simultaneous measurements of distances between the detector and the body, given by the sensors of the detector and by the antenna.

An embodiment of the invention may have one or more of the following:

a circuit for the automatic control of the speeds of the rotating arm and/or the arm and/or the post and/or the lift device on the basis of this reconstruction and of the distances measured, a circuit to regulate the intensity of the x-rays on the basis of this reconstruction and of the distances measured, a circuit to compute the time of exposure of a surface of the reconstructed body map to the x-rays, a circuit to compute an accumulated X-ray dose received by said surface.

the antenna comprising a plurality of capacitive electrodes made with a conductive material, the antenna being a flexible printed circuit made with an x-ray-transparent material such as plastic and the electrodes are made with a conductive material such as aluminum.

BRIEF DESCRIPTION OF THE DRAWINGS

Embodiments of invention will be understood more clearly from the following description and from the accompanying drawings. These figures are given purely by way of an indication and in no way restrict the scope of the invention. Of these figures.

DETAILED DESCRIPTION

Figure 2:
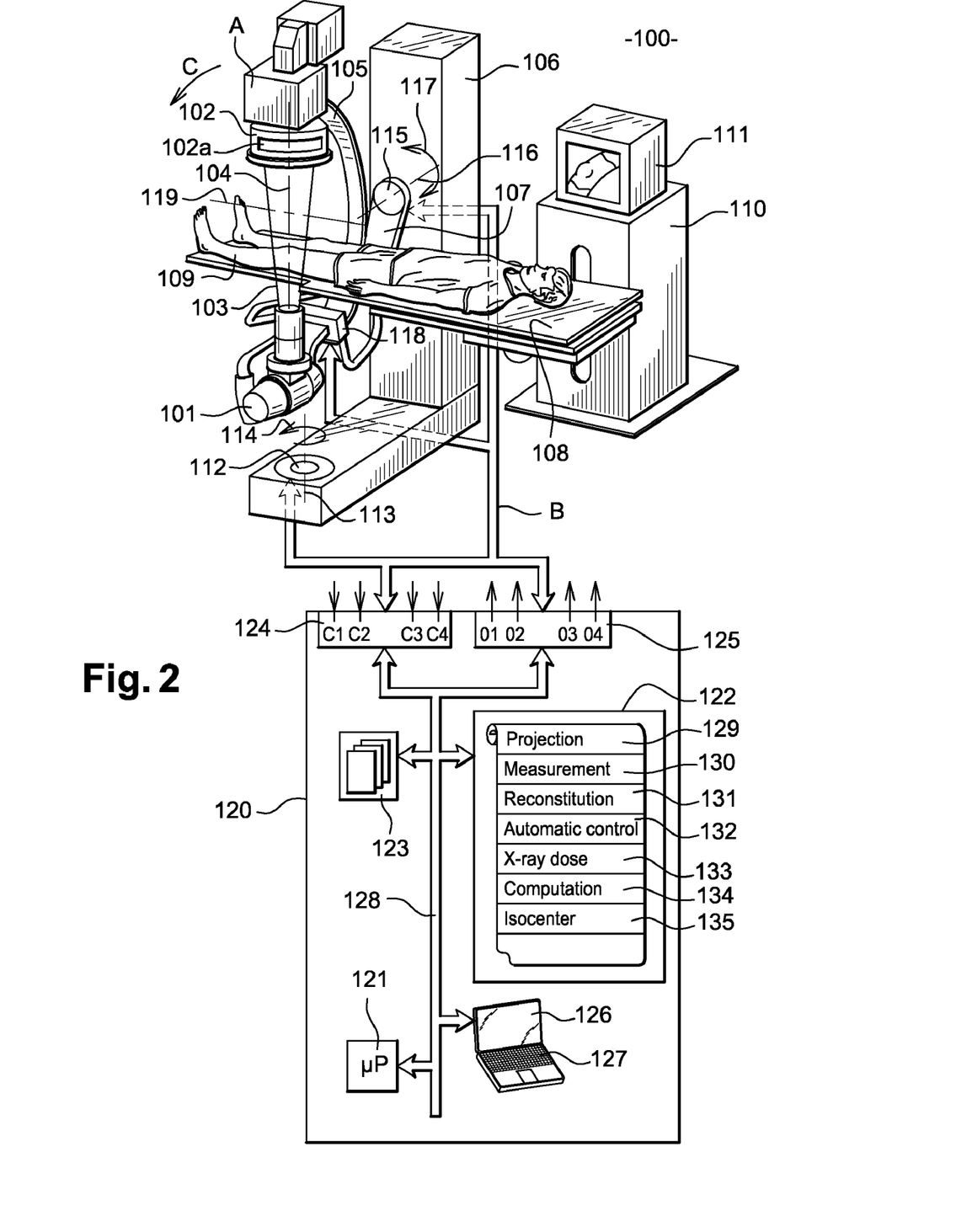
FIG. 2 is a schematic view of a vascular type of X-ray apparatus according to an embodiment of the invention.

FIG. 2 is a representation in space of a vascular type of X-ray apparatus 100 according to an embodiment of the invention. This apparatus 100 comprises for example an X-ray tube 101 as well as an X-ray detector 102. This tube 101 emits an X-ray beam 103 along a direction 104 of emission.

The tube 101 and the detector 102 are both hooked to the ends, on either side, of a C-arm 105. This arm 105, in the example of FIG. 2, is shaped like a hoop. The detector 102 is hooked to the arm 105 opposite the tube 101 and in the direction 104 of emission so as to receive the X-ray beam 103. The detector 102 is connected to a lift device A used to raise and lower said detector 102 in a direction of emission 104. The lift device A is connected to the arm 105.

The arm 105 is connected to an L-shaped post 106 by means of a rotating arm 107. A collimator situated at the end of the tube 101 can be used to convey a shape to the X-ray beam 103 emitted by the tube 101. Thus, this collimator could in particular modify the width of the beam 103.

The X-ray apparatus also has an examination table 108 on which a patient 109 is reclining. This examination table 108 is fixed and hooked to a frame 110. This examination table 108 is placed within the C-arm 105 so that the tube 101 is situated beneath the examination table 108 and the detector 102 is placed above the examination table 108. Whatever the examination made, the tube 101 and the detector 102 preferably always maintain this spatial configuration. In certain examinations, the tube 101 may be placed above the examination table 108 and the detector 102 beneath the examination table 108.

Thus, after having received the beam 103 which goes through a part of the patient's body, the detector 102 emits electrical signals corresponding to the intensity of the rays received. These electrical signals can then be transmitted to a computer 111 by means of wire links (not shown). These electrical signals can be used by this computer 111 to produce an image corresponding to the part of the body analyzed. This image can be viewed through a screen of this computer 111 for a radioscopy, or printed on a sheet for a radiography operation.

In order to enable a study of each part of the body of the patient 109, the beam 103 may be oriented in a multitude of directions about the patient. Indeed, the position of the tube 101 and of the detector 102 may be modified by a user. To this end, the L-shaped post 106, the rotating arm 107 and the C-shaped arm 105 are all three hinged in a pivoting position relative to one another.

More specifically, the L-shaped post is hinged and pivots on the ground by means of a first motor 112. This motor 112 thus enables the post 106 to rotate about a vertical axis 113. In a particular embodiment, the post 106 may rotate about the patient 109 at an angle 114 ranging from −100 degrees to +100 degrees.

The rotating arm 107 is hinged and pivots about the post 106 by means of a second motor 115. This second motor 115 enables the rotating arm 107 to rotate about a horizontal axis 116 which is perpendicular to a face of the post 106. In a particular embodiment, the rotating arm 107 may rotate about this axis at an angle 117 ranging from −117 degrees to +105 degrees.

The arm 105 may slide about a link 118. Thus, the arm 105 may rotate about an axis 119 which passes through the centre of a disk described by two C-arms placed side by side. This axis 119 is furthermore perpendicular to the axis 116 and to the axis 113 for the position shown.

Combining the motions of rotation about the three axes 113, 116 and 119, the link 118 enables the rays of beam 103 to describe all the directions of emission of the x-rays included within a sphere. Through the motors 112 and 115 and the link 118, the beam 103 can go through each part of the patient along a multitude of possible orientations.

As a variant, it is possible to use more than two motors of the 112 or 115 type so as to further increase the number of degrees of freedom of the apparatus 100. Increasing the degrees of freedom of this system facilitates the shifting of the tube 101 and of the detector 102. It is thus possible to reach a precise given position in several different ways.

The detector 102 has sensors 102a placed on its rim. These sensors 102a enable the apparatus 100 to be provided with information comprising at least one measurement of distance between the detector 102 and the parts of the body of the patient 109 not situated in the field of the X-ray beam 103.

The sensors 102a are preferably of a capacitive type. Other types of sensors may be used, for example optical, ultrasonic or infrared type sensors.

The capacitive sensors 102a enable the patient to undergo detection through a covering sterile sheet. The use of this type of capacitive sensor considerably reduces the number of sensors present on the detector 102. The sensors 102a do not have any filtering circuit because the sterile sheet covering the patient 109 does not disturb the measurements of said sensors. With this capacitive detection, the sterile sheet covering the patient 109 is not detected by the sensors 102a.

Figure 4:
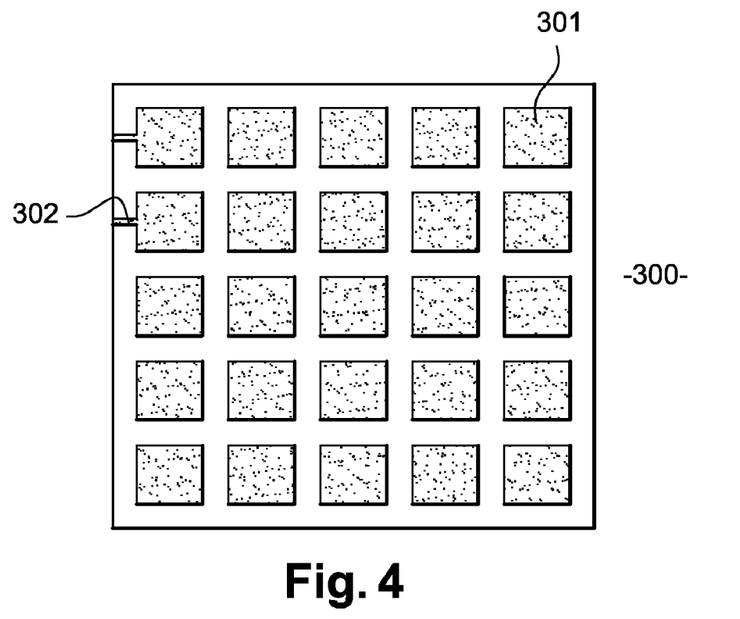
FIG. 4 is a schematic representation of an antenna according to an embodiment of the invention.

The detector 102 has an antenna on a face situated in the field of the X-rays. This antenna is shown in FIG. 4. The antenna is used to characterize the sector situated in the X-ray field between the detector and the patient's body map. In one example, the antenna characterizes a distance of 20 cm from the detector to the patient's body map in the field of the X-rays.

This antenna is designed to detect all the conductive objects placed in the x-ray field without affecting the quality of the image or disturbing or stopping the x-rays.

This antenna has electrodes. At each position of the moving parts about the patient, the electrodes, simultaneously with the sensors, measures a distance between the patient's body, and the detector. The electrodes are positioned in such a way in the antenna that they enable the measurement of the distances between the patient's body and the detector with a precision of about one centimeter when the detector is distant from the patient. The precision is in the range of one millimeter when the detector is near the patient. Thus, the closer the detector comes to the patient, the greater the precision of measurement of the distances and the greater the precision of reconstruction of the body map.

The measurements made by the capacitive sensors and the electrodes of the antenna are transmitted to a control logic unit 120 in the form of electrical signals, by means of an external bus B. The electrical signals enable this control logic unit 10 to reconstruct a 3D image by learning in a data base of images, this 3D image corresponding to the patient's body map. This image enables the control logic unit 120 to have knowledge, at each point in time, of the position of the patient's body relative to the detector 102 in order to set up an automatic control link accordingly for the moving parts of the x-ray apparatus 100, set up an automatic control link for a detecting position distance of the detector, compute an accumulated X-ray dose for each sector of the exposed body map and regulate the x-ray dose received by the patient.

In one example, this control logic unit 120 comprises a microprocessor 121, a program memory 122, a data memory 123, a display screen 126 provided with a keyboard 127 and an input-and-output interface 124 and 125. The microprocessor 121, the program memory 122, the data memory 123, the display screen 126 provided with a keyboard 127 and the input-and-output interface 124 and 125 are interconnected by an internal bus 128.

In practice, when an action is attributed to a device, it is carried out by a microprocessor of the device controlled by instruction codes recorded in a program memory of the device. The control logic unit 120 is such a device. This control logic unit 120 is often made in integrated-circuit form.

The program memory 122 is divided into several zones, each zone corresponding to instruction codes to fulfill one function of the device. Depending on the variants of the invention, the memory 122 has a zone 129 comprising instruction codes to set up a trajectory of the tube 101 and to command a multiplicity of projections along this trajectory. The memory 122 has a zone 130 comprising instruction codes to order the sensors and electrodes of the antenna to perform preferably simultaneous measurements of distance between the detector and the patient's body. The memory 122 has a zone 131 comprising instruction codes to carry out a volumetric reconstruction of the patient's body map. The memory 122 has a zone 132 comprising instruction codes to set up an automatic control link for the automatic control of the speeds of the mobile parts of the x-ray apparatus 100 and the detecting position distance of the detector in order to obtain better radiography image quality.

The memory 122 has a zone 133 comprising instruction codes to regulate the intensity of the x-rays to be applied to the patient for a radiology examination according to the distances measured at the zone 130 and of the reconstruction of the patient's body. The memory 122 has a zone 134 comprising instruction codes to measure the time of exposure to x-rays for each incidence or projection and compute the accumulation of x-ray dosage for the exposed body skin surface. The memory 122 has a zone 135 comprising instruction codes to automatically place the organ to be examined at the isocenter of the x-ray apparatus, on the basis of the reconstruction of the patient's body.

The control logic unit 120 is a speed control system enabling the automatic control, on the basis of information delivered by the different sensors 102a and the electrodes of the antenna, of the speeds of the arm 105 and/or the post 106 and/or the rotating arm 107 and/or the lift device A of the x-ray apparatus 100. The control logic unit 120 is a system of regulation of the dose received by the patient in optimizing the measurements of the distance between the elements of the x-ray apparatus 100 and the skin of the patient 109. The control logic unit 120 is also a system for setting up an automatic control over the position distances of the detector according to the image quality to be obtained, the approach speed of the lift device A and the reconstruction of the body map. The control logic unit 120 is a system for computing an accumulation of x-ray dosage for the patient's exposed skin surface.

In a radiology examination, the practitioner actuates the commands C1 and/or C2 and/or C3 and/or C4 of the input interface 124, and the control logic unit then sends orders O1 and/or O2 and/or O3 and/or O4 on the output interface 125, these orders corresponding to the actuated commands. These orders O1, O2, O3, O4 are used to actuate respectively the putting into motion of the motor 112, the motor 115, the link 118, the lift device A. The motor 112 shifts the post 106 about the axis 113, the link 118 shifts the arm 105 about the axis 119 and the lift device A shifts the detector 102.

Figure 3:
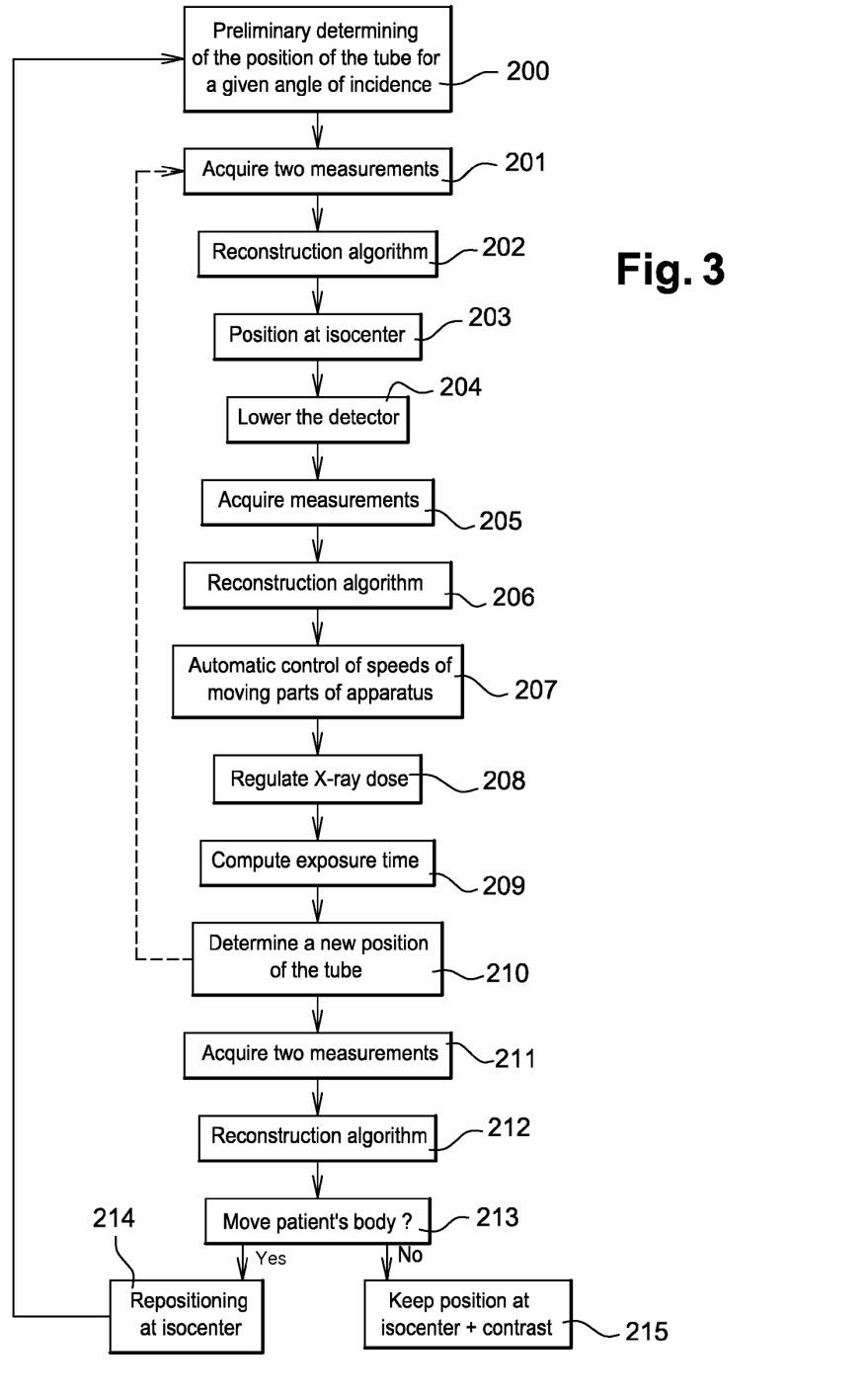
FIG. 3 illustrates means implementing a method provided according to an embodiment of the invention.

FIG. 3 illustrates means implementing a method provided by an embodiment of the invention. For example, in one implementation, a method of reconstruction of the patient's body is obtained from data given directly by the digital detector to the control logic unit.

Referring to FIG. 3, at the step 200, the practitioner actuates the commands C1 and/or C2 and/or C3 and/or C4 for a given incidence. The control logic unit applies the step 201 in which it sends the sensors and the ray antenna an order for the measurement of the distance between the detector and the patient's body, preferably as an absolute value. The control logic unit acquires the measurements simultaneously.

As soon as the first two measurements are obtained, the control logic unit applies the step 202. At the step 202, the control logic unit applies an algorithm for reconstruction of the patient's body map. This reconstruction algorithm is obtained by learning in a data base, using for example a decision tree, a neural network or else support vector machines. To perform this reconstruction, the control logic unit transmits the measurements of the distances to the image learning base which assigns a measured distance to each pixel of the body. The learning base outputs parameters for the 3D reconstruction of the body map.

In fact, prior knowledge of the patient's shape, which is unique, and of the spatial position of the examination table, the tube and the detector enables the reconstruction of the patient's body from the distance measurements.

The control logic unit gives a coarse reconstruction of the patient's body map from these first two distance measurements made by the sensors and the antenna.

At the step 203, the control logic unit uses the coarse reconstruction of the patient's body map to place the organ to be examined directly at the isocenter of the x-ray apparatus. This enables the elimination, firstly, of the repositioning time which lasts more than two minutes in the prior art. Secondly, it removes the need for the x-ray dose required to place the organ to be examined at the isocenter.

At the step 204, the lift A is lowered towards the patient 109. During this descent, the sensors and the antenna of the detector continue to perform simultaneous measurements of distance, preferably absolute distance, between the detector and the patient's body.

At the step 205, the measurements made at the step 204 are transmitted to the control logic unit. The closer the detector conservation body, i.e. the further the absolute value of the distance diminishes, the stronger is the signal received by the control logic unit.

At the step 206, the control logic unit applies the reconstruction algorithm to each new measurement acquired by the detector. The greater the number of measured distances given by the detector to the control logic unit, the finer the reconstruction of the body map. For, there is more data available to augment the precision of reconstruction of the patient's body map.

At the step 207, the control logic unit sets up an automatic control over the speeds of the arm 105 and/or the post 106 and/or the rotating arm 107 and/or the lift device A of the x-ray apparatus according to the reconstruction of the patient's body and measured distances. The control logic unit dictates the following on the x-ray apparatus: the slowing down or die continued acceleration or the stopping of the arm 105 and/or the post 106 and/or the rotating arm 107 and/or the lift device A. The fact that this deceleration of the speed of the lift device A is performed by the control logic unit optimizes the time for which the lift device remains at maximum speed. It also reduces the risks of collision between the detector and the patient 109 to the minimum.

At the step 207, the control logic unit also sets up an automatic control over the detecting position distances of the detector according to the approach speed of the lift device A, the image quality to be obtained and the reconstruction of the body map. The control logic unit thus makes it possible to determine an optimum detecting position distance of the detector. In this optimum position distance, the detector is as close as possible to the patient without in any way thereby coming into collision with the patient while at the same time enabling optimum radiography image quality.

As soon as the x-ray apparatus is at the right incidence, i.e. as soon as the detector is at an optimum detecting position distance, the practitioner actuates a command in order to trigger the emission of x-rays. Consequently, the x-ray tube emits x-ray intensities, more commonly called an x-ray dose, going through the patient's body for an examination. These x-ray intensities are emitted by the tube in the form of an x-ray beam. A collimator mounted on the tube is used to determine the size of the x-ray beam.

At the step 208, the control logic unit regulates the dose received by the patient. To this end, the control logic unit computes the thickness of the patient. This thickness is computed on the basis of the measured distances and the reconstruction of the body map. The regulation of the dose is done according to the reconstruction of the patient's body map and the computed thickness of the patient.

At the step 209, the control logic unit computes the accumulated x-ray dose on each exposed skin surface of the patient. To this end, the control logic unit measures a time of exposure to x-rays for a reconstructed body map sector situated beneath the x-ray beam. Depending on the size of the beam and the measured exposure time, the control logic unit computes the accumulated x-ray dose for this sector of the body map. This accumulated dose of x-rays must be limited in the course of one examination because, beyond a certain quantity, x-rays become mutagenic agents.

Computing the accumulated x-ray dose for an exposed sector makes it possible, without lowering the quality of the image, to determine the instant at which the tube must be shifted towards a new sector of the patient's body map. This makes it possible, for example, during a surgical operation when the exposure time is generally quite lengthy, to know the critical time of the dosage received by the patient for a part of the patient's body.

At the step 210, the control logic unit raises the detector and shifts the tube to a new angle of incidence about the organ to be examined. In certain radiography examinations, the control logic unit returns to the step 201 in order to obtain a new radiography image of the organ to be examined.

In the case of an image subtraction examination, the control logic unit applies the steps 211 to 215. The radiography image given by the control logic unit at the step 209 is in this case commonly called a mask image.

At the step 211, the control logic unit transmits an order to the sensors and to the antenna for the measurement of distance between the detector and the patient's body.

As soon as two first measurements have been obtained at this new incidence, the control logic unit applies the step 212. At the step 212, the control logic unit applies the algorithm for the reconstruction of the patient's body map.

The control logic unit gives a coarse reconstruction of the patient's body from these first two measurements of distance performed by the sensors and the antenna.

At the step 213, the control logic unit verifies the possibility of a shift between the new reconstruction of the patient's body map obtained at the step 212 and the old reconstruction of the patient's body map obtained at the steps 202 and 206.

When the two body maps are not in the same position relative to each other, then the control logic unit applies the step 214. If not, it applies the step 215.

At the step 214, the control logic unit again applies the steps 200 to 213 until the two body maps are in the same position. At the step 215, the control logic unit injects a contrast product into the patient's body relative to the organ to be examined. The control logic unit gives a new radiography image of the organ to be examined with the contrast product.

The control logic unit subtracts the radiography image obtained without injection of contrast product and the radiography image obtained with the contrast product. This subtraction gives the practitioner a final image that is more suited to analysis.

The images thus obtained are interpreted by the specialist practitioner in order to perform a diagnosis or as an aid in the performance of surgical operations.

For the patient, embodiments of the invention are aimed at increasing his or her safety, the speed of the examination, and his or her postural comfort. For the practitioner too, embodiments of the invention are aimed at increasing safety, image quality, speed, ergonomic quality and comfort of use.

This type of x-ray apparatus reduces the degree of pressure on the practitioner during the movement of the arm 105 and/or the post 106 and/or the rotating arm 107 and/or the lift device A around the patient. The fact that the speed of the arm 105 and/or the post 106 and/or the rotating arm 107 and/or the lift device A are dictated by the control logic unit considerably reduces action on the part of the practitioner on the speed commands for the movements, while at the same time increasing the productivity of the x-ray apparatus 100.

Embodiments of the invention optimizes the time taken to position the detector close to the patient without any risk of injuring the patient when the rotating arm 107 and/or the post 106 and/or the arm 105 are at maximum speed. It thus sets up an automatic control over the approach speed of the detector and regulates the dose of x-rays received by the patient.

FIG. 4 shows an example of a schematic representation of an antenna. The antenna 300 is placed on one face of the detector situated in the field of the x-rays. The antenna 300 is made of an x-ray-transparent material, plastic for example. The antenna 300 is a flexible, multilayer printed circuit. The antenna has at least two electrodes 301. In the example of FIG. 4, the antenna 300 has 25 electrodes 301.

The electrodes 301 are printed on the plastic film of the antenna 300 according to a predetermined geometry. This geometry is determined according to the measurements to be obtained and the organs to be detected. These electrodes are oriented in several axes in order to cover all the useful zones. In the example of FIG. 4, the electrodes 301 form a regular grid. In one variant, they may form an irregular grid. The electrodes 301 may have different sizes. In the example of FIG. 4, the electrodes 301 all have the same size.

As many antennas as possible may be placed in the X-ray field in order to increase the precision of the measurements. The greater the number of electrodes, the higher will be the resolution of the measurements. Furthermore, the combination of several electrodes with several plastic films improves the resolution of the distance measured.

The surface area of the electrode 301 gives the precision of the distance measured. Thus, for a surface area of 36 cm$^2$, i.e. an electrode having a 6-centimeter side, the distance of the measurements may attain 15 cm with precision of 1 cm, when the detector is at a distance from the patient. The closer the detector comes to the patient's body, the greater the increase in precision, which may become millimetric.

The control logic unit simultaneously commands the measurements of the distance between the antenna 300 and the patient's body by the electrodes 301. These measurements are sent to the electronic board through the conductive tracks 302. Finally, the electronic board transmits the measurements made to the control logic unit. These measurements are combined with the measurements made by the capacitive sensors of the cover in order to reconstruct the patient's body map, thus enabling automatic control of the approach speeds of the tube and/or of the detector, automatic control of the distances between the detector and the reconstructed body map, the computation of the accumulated x-ray dose for each exposed skin surface of the patient, and the regulation of the x-ray dose.

The electrodes of the antenna and the sensors of the detector form the equivalent of a pixel camera in which each pixel is constituted by one electrode. This camera shifted along the patient's body will enable the building of a 3D reconstruction of the patient's body map by a learning process.

What is claimed is:

1. A method of 3D reconstruction of a body map, the method comprising:
   shifting an arm of an x-ray apparatus along a trajectory relative to a body, the x-ray apparatus bearing an x-ray tube and a detector being situated so as to be opposite the tube, the detector fixed to a lift device, the lift device connected to the arm;
   lowering the lift device and the detector towards the body;
   measuring distances between the detector and parts of the body situated outside a field of x-rays, using sensors placed on a rim of the detector;
   automatically controlling a speed of approach of the lift device relative to the body according to these measured distances;
   measuring distances between the detector and body parts of the body situated in the field of x-rays, using an antenna on one face of the detector;
   transmitting the measured distances between the detector and the parts of the body situated in the x-ray field and the measured distances between the detector and the parts of the body situated outside the x-ray field to an image learning base which assigns a measured distance to each pixel of the body; and
   outputting 3D reconstruction parameters of the body map based at least in part on the measured distance to each pixel of the body.

2. A method according to claim 1, further comprising:
   computing a speed of approach of the detector to the body from the measured distances; and
   automatically controlling speed of the motions of the lift device according to the computed speed of approach and the 3D reconstruction of the body map.

3. A method according to claim 1, further comprising:
   automatically controlling a detecting position from the detector to the body according to a risk of collision between the detector and the 3D reconstruction of the body map.

4. A method according to claim 1, further comprising:
   determining, depending on the 3D reconstruction of the body map, a thickness of the body; and
   regulating an intensity of the x-rays received by the body according to the thickness of the body and the distances measured.

5. A method according to claim 1, further comprising:
   measuring two distances between the detector and the body without x-ray emission; transmitting these measurements to the learning base, giving a coarse 3D reconstruction of the body map at output; and
   placing an organ to be examined at an isocenter of the x-ray apparatus, according to the coarse 3D reconstruction of the body map.

6. A method according to claim 1, further comprising:
   placing the tube or the body in a predetermined position according to an examination to be undertaken;
   emitting with the tube, an x-ray beam having a size defined by a collimator of the tube on a reconstructed body map;
   measuring a time of exposure of this surface to the x-ray beam; and
   computing the accumulated dose of x-rays on said surface according to the measured time of exposure and the size of the x-ray beam.

7. A method according to claim 1, further comprising:
   placing, in an examination requiring a subtraction of images, the tube of the body in a position predetermined according to the examination to be undertaken;
   determining a first reconstruction of the external envelope of the body;
   producing a first radiography image of the body from the x-rays detected by the detector;
   determining a second reconstruction of the body map;

comparing the first reconstruction of the body map with the second reconstruction of the body map;

wherein, if the second reconstruction of the body map has shifted relative to the first reconstruction of the body map, then determining a new radiography image and a new reconstruction of the body map and comparing this new reconstruction of the body map with the second reconstruction of the body map;

wherein if the second reconstruction of the body map has not shifted relative to the first reconstruction of the body map, injecting a contrast product into the body, determining a second radiography image of the body, and comparing the first radiography image with the second radiography image to facilitate medical analysis.

8. An X-ray apparatus, comprising:

an x-ray tube configured to emit an x-ray beam along a direction of emission;

an x-ray detector situated so as to be opposite the x-ray tube, the detector having a face situated in the direction of emission;

a lift device configured to raise and lower the x-ray detector in the direction of emission;

an arm bearing the x-ray detector and the x-ray tube;

a post connected to the arm by means of rotating arm;

sensors placed on a rim of the detector and an antenna on the face of the detector, wherein the apparatus has a circuit configured to generate a 3D reconstruction of a body using at least data obtained from an image learning base, on a basis of simultaneous measurements of distances between the detector and the body, given by the sensors and by the antenna.

9. An apparatus according to claim 8, further comprising a circuit for the automatic control of the speeds of the rotating arm and/or the arm and/or the post and/or the lift device on the basis of the 3D reconstruction and the distances measured.

10. An apparatus according to claim 8, further comprising
a circuit to regulate the intensity of the x-rays on the basis of the 3D reconstruction and the distances measured,
a circuit to compute the time of exposure of a surface of the reconstructed body map to the x-rays,
a circuit to compute an accumulated X-ray dose received by said surface.

11. An apparatus according to claim 8, wherein:
the antenna comprises a flexible printed circuit including an x-ray-transparent material such as plastic, and also comprises a plurality of capacitive electrodes including a conductive material.

\* \* \* \* \*

UNITED STATES PATENT AND TRADEMARK OFFICE
CERTIFICATE OF CORRECTION

PATENT NO. : 7,693,263 B2
APPLICATION NO. : 11/831991
DATED : April 6, 2010
INVENTOR(S) : Bouvier et al.

It is certified that error appears in the above-identified patent and that said Letters Patent is hereby corrected as shown below:

Title Page, Item (75), "Inventors", in Column 1, Line 1, delete "Erangy-sur-Oise" and insert -- Eragny-sur-Oise --, therefor.

In Column 1, Line 18, delete "or" and insert -- of --, therefor.

In Column 9, Line 37, delete "die" and insert -- the --, therefor.

In Column 12, Line 30, in Claim 3, after "position" insert -- distance --.

Signed and Sealed this

Twenty-fourth Day of August, 2010

David J. Kappos
*Director of the United States Patent and Trademark Office*